United States Patent [19]

Koganty

[11] Patent Number: 5,055,562

[45] Date of Patent: Oct. 8, 1991

[54] FLUOROCARBON CHAIN-CONTAINING ANTIGENIC CONJUGATES

[75] Inventor: R. Rao Koganty, Edmonton, Canada

[73] Assignee: Biomira, Inc., Alberta, Canada

[21] Appl. No.: 151,145

[22] Filed: Feb. 1, 1988

[51] Int. Cl.[5] ............................................. C07K 17/02
[52] U.S. Cl. .................................. 530/403; 530/389;
530/390; 530/391; 530/404; 530/405; 530/406;
530/408; 530/409; 530/410
[58] Field of Search ............... 530/403, 404, 405, 389,
530/390, 391, 406, 408, 409, 410

[56] References Cited

U.S. PATENT DOCUMENTS

| | | | |
|---|---|---|---|
| 3,133,908 | 5/1964 | Klevens | 530/408 |
| 4,228,274 | 10/1980 | Ponpipom et al. | 536/4 |
| 4,259,324 | 3/1981 | Ponpipom et al. | 424/180 |
| 4,301,152 | 11/1981 | Ponpipom | 424/182 |
| 4,433,051 | 2/1984 | Gilad et al. | 435/7 |

FOREIGN PATENT DOCUMENTS 98252 1/1984 European Pat. Off. .

OTHER PUBLICATIONS

Kovac et al (1985) J. Carbohydrate Chemistry 4(4):613–626.
Riess et al. (1978) Angew. Chem. Int. Ed. Engl. 17(9):621–700.
von Werner et al. (1981) J. Fluorine Chem. 19:163–180.
Gerstenberger and Haas, Angew. Chem. Int. Ed. Engl., 20:647–667 (1981).
Bovin, Chem. Abst. Selects: Carbohydrates (Chemical Aspects), 106:102617f.
Duschinsky and Pleven, Heidelberger, J. Amer. Chem. Soc. 79:4559 (1957).
Gottwald, et al., J. Biol. Chem., 239:435 (1964).

Primary Examiner—Jeffrey E. Russel
Assistant Examiner—Kay Kim
Attorney, Agent, or Firm—Iver P. Cooper

[57] ABSTRACT

Fluorocarbon chain-containing linking arms can be used to conjugate haptens to protein carriers such as BSA, HSA, or antibodies without recourse to harsh chemistry. In addition, $^{19}$F atoms serve as markers for quantitative estimation of bound haptens.

24 Claims, No Drawings

FLUOROCARBON CHAIN-CONTAINING ANTIGENIC CONJUGATES

BACKGROUND OF THE INVENTION

1. Field of the Invention

This invention relates to fluorocarbon chain linking arms and their use in conjugating haptens or drugs to carriers.

An antigen is a substance which may be recognized by an antibody. An antigen that elicits a response from the immune system is called an immunogen. Macromolecular molecules such as proteins or nucleic acids are usually immunogenic in a xenogeneic host; molecules with a molecular weights less than 5000 are usually not. However, many small non-immunogenic substances will stimulate an immune response if covalently attached to a large carrier molecule; such substances are termed haptens. A hapten can be recognized and bound by an antibody even though it cannot stimulate antibody production itself. Linking a haptenic substance to carriers results in a molecule generally referred to as synthetic antigen. This invention relates to a novel linker connecting the synthetic antigens with hapten to its carrier.

Several linking arms are known for conjugating haptens to carriers. See Kolar U.S. Pat. No. 4,442,284; Lemieux U.S. Pat. No. 4,137,401; Feizi U.S. Pat. No. 4,563,445; Svenska Sockerfabrike, EP Appl 98,252; Behringerwerke AG, EP Appl 60,999. None of these linking arms, however, contain fluorocarbon chains.

An extensive review of methods of fluorinating organic compounds and of uses of fluorinated organic compounds appears in Gerstenberger and Haas, Angew. Chem. Int. Ed. Engl , 20: 647–667 (1981), incorporated by reference herein. Nowhere does it even suggest that fluorinated compounds have utility as "spacers" in immunological conjugates.

Klevens U.S. Pat. No. 3,133,908, teaches binding fluorinated aliphatic acids, alcohols and their derivatives or amines to a proteinaceous material to protect the latter from denaturation. He does not, however, disclose use of the fluorinated compound as a bridging agent.

Ponpipom U.S. Pat. No. 4,259,324 describes an "immunologic adjuvant" having the structure Y-R, where Y is one of three thio glycosides and R may be 3-[(p-tetrafluorophenethyl) phenyl] propyl. This side chain is not used to couple the glycoside to another molecule. See also Ponpipom U.S. Pat. No. 4,301,152 and U.S. Pat. No. 4,228,274.

Bovin, Chemical Abstracts Selects Carbohydrates (chemical Aspects), 106: 102617f teaches a synthesis of a T-antigen disaccharide with an $-O(CH_2)_3NHCOCF_3$ moiety, without disclosing use of this moiety as a linker. Moreover, only one carbon atom is fluorinated.

One of the glycosides described in Svenska Sockerfabrike, EP Appl 98,252 is (sugar)$_{1-10}$—O—(CH$_2$)$_{2-20}$-Hal (see page 7). This compound is used as an intermediate in the preparation of various O-glycosides. There is no disclosure of use of this omega-haloalkyl glycoside as a linking arm. Only one carbon atom is fluorinated.

Duschinsky and Pleven, Heidelberger, J. Amer. Chem. Soc., 79: 4559 (1957) describe the preparation of 5-fluoropyrimidines.

Gottwald, et al., J. Biol Chem., 239: 435 (1964) discuss the chemical synthesis and enzyme-inhibitory activity of alpha-monofluoroglutaric acid.

Gilad, U.S. Pat. No. 4,433,051, refers to alphadifluoromethylornithine derivatives.

No admission is made that any of the foregoing constitute more than information which applicants thought might be of interest to an examiner.

SUMMARY OF THE INVENTION

This invention relates to the use of linking arms containing at least one fluorinated aliphatic carbon chain to couple a biologically active substance to a carrier. The carrier preferably bears an amino function whereby it may be coupled with the linker, and is preferably a protein. The biologically active substance may be a hapten, in which case the carrier is selected so as to render the resulting conjugate immunogenic. It may also be a drug or toxin, in which case the carrier is a cell targeting and/or internalization agent such as an antibody for a cell surface antigen.

One problem in the development of immunoassays for hapten is that the antibody elicited by a conjugate of a hapten and a protein carrier may recognize an epitope formed jointly by the hapten and the carrier, rather than one limited to the hapten. Fluorocarbons may be immunologically inert, as I have inferred from their successful use as blood substitutes. Riess and LeBlanc, Angewandte Chemie 17: 621–34 (1978). Hence, the use of a fluorocarbon to link hapten to a protein carrier renders it less likely that the screening antibody will bind to an adventitious epitope.

Fluorinated linking arms may also act as labels for haptens whereby the number of hapten molecules bound to a single carrier protein molecules may be determined. This is possible because of the distinctive nuclear spin ($I=\frac{1}{2}$) of fluorine. The F atoms may be detected by NMR spectroscopy or neutron activation analysis, of which the former is nondestructive. In contrast, the phenol-sulfuric acid method of hapten substitution determination destroys the conjugate. Dubois, et al., Analytical Chem.: 28, 350 (1956).

Fluorinated linking arms are also useful for linking drugs or toxins to cell targeting agents such as specific antibodies or lectins. Drug-antibody conjugates are disclosed in Goers, WO 86/01720; Casellas, U.S. Pat. No. 4,643,895; Urnovitz, EP Appl 193,161; Scannon, U.S. Pat. No. 4,590,071; Neville, Jr., U.S. Pat. No. 4,440,747. The high energy of the C-F bond (107 kcal/mole), makes fluorocarbons resistant to metabolic activity, and indeed they are regarded as "antimetabolites."

Fluorocarboxyl esters are particularly useful for conjugating other molecules to receptor proteins (e.g., antibodies) since such esters can react with proteins, without addition of chemical coupling agents, through an amide linkage. Harsh conjugation conditions (acyl azide, schiff base, etc.), may undesirably alter the substances to be conjugated.

The novel compounds contemplated by the present invention include the final hapten-linking-arm-carrier conjugates, as well as the intermediate hapten-linking or linking arm-carrier constructions.

The appended claims are hereby incorporated by reference as a further description of the preferred embodiments.

For the purpose of appended claims the term "fluorocarbon chain" shall mean a sequence of at least two carbon atoms in which at least two aliphatic carbon atoms are at least partially fluorinated.

DETAILED DESCRIPTION OF THE PREFERRED EMBODIMENTS

The fluorinated linking arm of the present invention comprises one or more chains of fluorinated aliphatic carbon atoms. Each chain may be partially or wholly fluorinated, and the same is true for individual carbon atoms in the chain. The linking arm may also include one or more chains of unfluorinated aliphatic carbon atoms, as well as one or more —O—, —CO—, —S— and/or —NH— linkages. The following non-limiting examples illustrate some of the contemplated linking arms, wherein m, n, p and q are each at least 1 and R is H or active group whereby the linking arm may be attached to a protein:

(a) —$(CH_2)_m$—$(CF_2)_n$—R';
(b) —$(CH_2)_m$—$(CF_2)_n$—$(CH_2)_p$—R';
(c) —O—$(CH_2)_m$—$(CF_2)_n$—R';
(d) —O—$CH_2)_m$—NHCO—$(CF_2)_n$—R';
(e) —$(CH_2)_m$—$(CF_2)_n$—$(CH_2)_p$—$(CF_2)_q$—R';
(f) —$(CH_2)_m$—O—$(CF_2)_n$—R'; and
(g) —O—$(CH_2-CF_2)_n$—R'

R' may be —$CON_3$, —$N_3$, —$CONHNH_2$, —$NHNH_2$, —$NH_2$, —OH, —OMe, —OEt, —O—Benzyl, —COOMe, —COOEt, —COO—Benzyl or —$CF_3$.

Usually, m, n, p and q are in the range 2–20.

Example 1: Preparation of Gal—O—$CH_2$—$(CF_2)_3$—COOMe

An example of the preparation of a hapten conjugated to a fluorinated linking arm, as contemplated herein, appears below.

1. Hexafluoroglutaric acid monomethyl ester: 12.0 g (50 m mole) of Hexafluoroglutaric acid and 2.4 g (75 m mole) of dry methanol were heated at 60° C. for 2 hours. Excess methanol was distilled off at normal pressure and the residue was fractionated at reduced pressure. 3.5 g of dimethyl ester was collected at 55° C. at 2.5 mm/Hg followed by 7.5 g (60%) monomethyl ester at 90°–92° C. Dimethyl ester can be obtained in 80% yield by heating with large excess of dry methanol. NMR in $CDCl_3$ shows a sharp singlet at 3.65 for monomethyl ester and a sharp singlet at 3.71 for dimethyl ester.

2. 2,2,3,3,4,4—Hexafluoro, 5-Hydroxy pantonoic acid methyl ester:—5 ml of $BH_3$ THF (1M) was gradually added to a solution of 1.0 g (4 mmol) hexafluoroglutaric acid monomethyl ester and 0.2 g of triethyl amine in 50 ml of dry THF cooled to −15° C. and stirring. Stirring was continued for 2 hours at −15° C. and for 4 hours at room temperature. 5 ml of ethanol and 1 ml of acetic acid were added and stirred for 15 minutes. Solvent was removed under vacuum and the residue was suspended in 25 ml of water and neutralized with $Na_2CO_3$ solid to pH 7.5 to 8.0 and extracted with ether (3×50 ml). The combined extracts were dried and evaporated to dryness. The crude residue 0.55 g (about 50%) was stored under refrigeration and used without further purification. NMR ($CDCl_3$) delta 3.98 (s, 3H); 3.3 to 3.6 (m, 2H).

3. 5-0-Tetraacetyl galactosyl 2,2,3,3,4,4, hexofluoropentanoic acid methyl ester: To a stirring slurry of 0.2 g (0.8 mmole) of 5-hydroxy, 2,2,3,3,4,4 hexafluoropentanoic acid methyl ester, 1 gm of powdered molecular sieves, 1 gm of powdered dry $CaSo_4$, 1 gm of $Ag_2CO_3$ and 50 mg of $AgClO_4$ in 25 ml of dry methylene chloride, 0.5 g (1.2 m mole) of acetobromogalactose was added. After 6 hours of stirring, another 0.2 gm (0.5 m mole) of acetobromo galactose was added and stirred for 2 hours. TLC (3:2 hexane, ethyl acetate) showed completion of reaction. After filtering and removal of solvent, the crude substance was purified on silica gel column (3:2 hexane, ethyl acetate). The ester group was partially hydrolysed during column chromatography but was reesterified by stirring in dry methanol for 2 hours. 0.26 g (55%) of beta-glycoside was isolated. $H^1$ NMR ($CDCl_3$), 5.86 (d, J=9.5 Hz, 1H, H'); 3.62 (s, 3H, $CH_3$); 1.85–2.2 (4xs, 4 x $CH_3$); $C^{13}$, 140, 136 and 97.6. $F^{19}$ 43.7, 43.3 and 37.7 with reference to $C_6F_6$.

4. 5O-Galactosyl, 2,2,3,3,4,4-hexafluoropentanoic acid methyl ester: 0.14 gm (0.25 mmole) of tetracetyl glycoside 3 was deacetylated in 5 ml of methanol and 0.5 ml triethylamine for 6 hours. The crude product was purified using neutral alumina column using a solvent system of 65:35:5 ($CHCl_3$:MeOH:$H_2O$). Methyl ester of the glycoside was hydrolysed to free carboxylic acid during purification. NMR ($D_2O$) 4.31 (d, $9H_2$, H'); 4.1–3.5(m, 7H); 3.65(s, 3H, $CH_3$). $^{19}$F NMR 43.3–43.7(m, 4F); 37.7(m, 2F). $CF_3COONa$ was used as internal reference.

5. 5-N-(2'-Hydroxy ethyl) 2,2,3,3,4,4-hexafluoroolutaric amide monomethyl ester: To 4.0 g (15 m mole) of hexafluoroglutaric acid dimethyl ester in 25 ml of dry methanol. A solution of 0.61 g (10 m mole) of ethanolamine in 5 ml of dry methanol was added dropwise and stirred at 45° C. for 30 minutes. Upon removal of solvent and purification of the residue over a silica gel column (10% methanol in $CHCl_3$) 2.5 g (83%) of product was obtained as a colorless heavy oil. NMR (DMSO) 9.25(t, NH, $J^1$=6 Hz); 4.8 (t, OH, $J^2$=6.5 Hz); 3.45(m, 2H); 3.35(s, 3H, $CH_3$); 3.25(m, 2H).

6. 5-N-(Beta-2'-O-galactosyl ethyl) 2,2,3,3,4,4-hexafluoroglutaric acid methyl ester amide: To a solution of 0.15 g (0.5 mmole) of 5-N-(2'-hydroxy ethyl 2,2,3,3,4,4 hexofluoroglutaric amide monomethyl ester in 20 ml dry methylene chloride, 0.55 g (2 mmoles) of $Ag_2CO_3$, 20 mg $AgClO_4$ followed by 0.6 g (1.5 m mole) of acetobromogalactose were added. 0.5 g each of powdered molecular sieves and $CaSO_4$ were added and stirred for 15 hours under anhydrous conditions. TLC (3:2 hexane, ethyl acetate) indicated completion of reaction. The crude mixture was passed through a silica gel column to obtain nearly pure product (TLC). Deblocking was carried out without further purification in methanol: triethylamine (9:1). 0.11 g (50%) of product was purified (silica gel, 65:35:5 $CHCl_3$, MeOH, $H_2O$). NMR ($D_2O$), 4.36 (d, 1h, H', J=9 Hz); 4.1–3.3(m, 11H, singlet at 3.6, $CH_3$); 3.14 (m, 2H). $^{19}$F; 41.7 and 48.6 ($CF_3COONa$ as reference.) Methyl ester was partially deblocked during the deblocking.

Example 3: Preparation of Antigenic Conjugate

A fluorinated hapten as described above (compounds 4 and 6) was stirred with HSA in water for a period of 2 hours, and dialyzed in SPEC2RAORE membrane tubing for 72 hours against three changes of distilled water. The conjugates contained up to 30 haptens per mole of HSA, as determined in Example 4 below.

Example 4: $^{19}F$ NMR Analysis of Conjugates

Many nuclei act much like charged spinning bodies and therefore produce a magnetic moment along their axes of rotation. When such a nucleus is placed in a uniform magnetic field, it will try to align itself with the field. As a result, it will precess like a spinning top, at a particular quantized precession frequencies. Each allowed precession frequency is associated with an energy level known as a nuclear zeeman level. If an alternating field is placed perpendicular to the uniform field, the nucleus may be caused to resonate between two energy levels. The electronic environment of the nucleus alters the field strength at which the resonance occurs.

5–20 mg of a freeze dried conjugate was dissolved in 0.2 mL of $H_2O$ in a 5 mm NMR tube and 0.1 mL of $D_2O$ was added for deuterium signal lock. The spectra were recorded on Bruker AM-300 Model fourier transformation NMR spectrometer which operates at 300 MHz using a narrow bore supercooled magnet. The $^{19}F$ signals were quantified by adding a known quantity of $CF_3COONa$ (50 µl of 1 m solution in water) which also functions as an internal reference. Typically $^{19}F$ signals may be observed after 50–200 scans at a pulse width of 8.0 usec. Signal integration was carried out first by adding a known quantity of reference ($CF_3COONa$, purchased from Aldrich) and repeating this process a second time to minimize the error in addition of $CF_3COONa$. $^{19}F$ estimations are within 5% error range.

| COMPARISON OF ESTIMATES OF HAPTENS/MOLE OF HSA | | | | | |
|---|---|---|---|---|---|
| STRUCTURE NO. | HSA | REACTION TIME | $^{19}F$-NMR | NEUTRON ACTIVATION ANALYSIS | PHENOL SULFURIC ACID METHOD |
| 4 | 1:100 | 30 Mins | 14 ± 0.7 | 15 ± 3 | 15–22 |
| 4 | 1:100 | 2 Hrs. | 31 ± 1.5 | 29.5 ± 2 | 19–36 |
| 4 | 1:100 | 2 Hrs. | 34 ± 1.5 | N/A | 40–56 |

Thus, it is possible to use NMR to determine the average number of haptens on a single carrier molecule if the hapten is linked to the carrier by a fluorocarbon-containing chain as described and one or more fluorines are of isotope 19.

General application: To demonstrate that any hapten with a linking arm containing an amino function may be bound to a protein carrier using hexafluoroglutaric acid diester, a synthetic sequence as in Example 5 is carried out.

Example 5: Synthesis of 1(2'-amino ethyl) galactoside 7. 2-Hydroxyethyl phthalimide: 6.1 g (100 m mole) of ethanolamine and 14.8 (100 m mole) of phthalic anhydride are heated at 140°–150° C. for 2 hours with stirring. The melt was poured in cold water and extracted with $CHCl_3$ (3×150 ml). 16 g (84%) pure white crystalline solid, m.p. 128°–130° C. (lit m.p. 128° C.) was obtained.

8. 2-O-Tetraaceto galactosyl ethyl phthalimide:—To 0.3 g (1.5 mmol) of 2-hydroxy ethyl phthalimide in 25 ml of dry methylene chloride, dry molecular sieves and $CaSO_4$, 0.7 g (2.5 mmol) of $Ag_2CO_3$ and 50 mg were added. 0.7 g (1.5 mmol) of acetobromo galactose was added and stirred at room temperature for 4 hours. Another 0.35 gm (0.75 mmole) of acetobromogalactose was added and stirring continued for 15 hours. TLC (3:2 Hexane: ethyl acetate) shows completion of reaction. Purification over silica gel column (3:2 Hexane: ethyl acetate) gave 0.46 g (60%) of pure beta anomer. NMR ($CDCl_3$) 7.94(m, 2H); 7.8(m, 2H); 5.4(d, 1h, $H^4$, $J_{3,4}{}^1$=3.5 Hz); 5.2(dd, 1H, $H_2$, $J^2{}_{1,2}$=9.5 Hz, $J^3$=9, Hz); 5.0(dd, 1H, $H^3$); 4.52(d, 1H, $H^1$); 3.8–4.2 (m, 7H); 1.92–2.18 (4xs, $CH_3$x4, 12H).

9. 2-O–galactosyl ethylamine: - 0.26 g(0.5 mmol) of 2-O-tetraacetogalactosyl ethyl phthalimide in 5 ml of ethanol was refluxed with 0.1g of hydrazine for 2 hrs. TLC (65:35:5 of $CHCl_3$:MeOH:$H_2O$ ) indicated completion of the reaction. 0.16 g (68%) of pure deblocked material was purified over silica gel column (65:35:5:2 $CH_3C^{13}$, MeOH, $H_2O$, $Et_3N$). NMR ($D_2O$) 4.5 (d, 1H, H', J=9.5 Hz), 4.15–3.5(m, 8H), 3.1(m, 2H).

10. 5-N-(2'-O-Galactosylethyl amido), 2,2,3,3,4,4-hexafluoroglutaric acid methyl ester: 0.2 g of 2-O-galactosyl ethylamine acid dimethyl ester were stirred for 2 hours at room temperature in 5 ml dry methanol. Excess of methanol and glutamine diester were removed under vacuum. The residue was pure NMR ($D_2O$) 4.34 (d, 1H, $H^1$, J=9.5 Hz); 3.65 (s, 3H, $CH_3$); 4.05–3.1(m, 10H). $^{19}F(D_2O)$;−4.19(4F); −48.58(2F) ($CF_3COONa$ as internal reference).

This hapten was coupled to HSA as described earlier.

Example 6: Preparation of Synthetic T Antigen

In a typical experiment, 15 mg of synthetic T-hapten (Gal-GalNac-O($CH_2$)$_5$-$NH_2$), see e.g., Lemieux, EP Appl. 44, 188, was stirred with 0.5 g of hexafluoroglutaric acid methyl ester and 0.5 ml of dry methanol, at room temperature for 2 hours. Excess methyl ester and methanol was removed under vacuum. The residue was dissolved in 2 ml of water and slowly added to a solution of 60 mg of Keyhole Limpet Hemocyconin (KLH) in water. The protein solution was stirred at room temperature for 20 hours. The KLH-T conjugate was purified by chromatography (Biogel P-5DG, water). The following table provides analytical data on a series of conjugates that were made using the T-hapten (11).

| Carrier | Amount of Carrier (mg) | Amount of T-hapten (mg) | Amount of Conjugate | Ratio mole of T/carrier |
|---|---|---|---|---|
| HSA | 10 mg | 5 mg | 5 mg | 50 |
| KLH* | 15 mg | 20 mg | 20 mg | 8,000 |
| KLH* | 60 mg | 8 mg | 55 mg | 2,500 |
| KLH* | 60 mg | 15 mg | 60 mg | 4,500 |

*molecular weight of KLH was taken as 8 × 10$^6$

I claim:

1. A method of conjugating a hapten with an immunogenic carrier which comprises forming a conjugate of the hapten and the carrier covalently linked together by a linker comprising at least one fluorocarbon chain.

2. The method of claim 1, wherein the carrier bears an amino function.

3. The method of claim 1, wherein the carrier is a protein.

4. The method of claim 3 in which the linker is attached to the hapten by an amide linkage.

5. The method of claim 3 in which the linker is

H—Ch—(CH$_2$)$_m$—(CF$_2$)$_n$—R' where CH stands for chalcogen and is oxygen or sulfur, m is 2–20, n is 2–20, and R' is H or a reactive group that participates in the coupling of the linker to a protein.

6. The method of claim 3 where R' is selected from the group consisting of —CON$_3$ —N$_3$, —CONHNH$_2$,—NHNH$_2$, —NH$_2$, —OH, —OMe, —OEt, —COO—Benzyl and —CF$_3$.

7. The method of claim 3 in which the linker is

H—CH—(CH$_2$)$_m$—NHCO—(CF$_2$)$_n$—R' where Ch stands for chalcogen and is oxygen or sulfur, m is 2–20, n is 2–20, and R' is H or a reactive group that participates in the coupling of the linker to a protein.

8. The method of claim 5 where R' is selected from the group consisting of —CON$_3$, —N$_3$, —CONHNH$_2$, —NHNH$_2$, —NH$_2$, —OH, —OMe, —OEt, —COO—Benzyl and —CF$_3$.

9. The method of claim 3 in which the linker is attached to the hapten by an ether linkage.

10. The method of claim 3 in which the linker comprises at least two aliphatic carbon chains, at least one of which is fluorinated.

11. The method of claim 8 in which at least one pair of chains is coupled together by an ether, together, or amide linkage.

12. The method of claim 3 in which the linker portion of the resulting conjugate is essentially immunologically inert.

13. An antigenic conjugate comprises a hapten, an immunogenic carrier, and a covalent linker comprising at least one fluorocarbon chain.

14. The conjugate of claim 13, wherein the carrier bears an amino function.

15. The conjugate of claim 13, wherein the carrier is a protein.

16. The antigenic conjugate of claim 15, wherein the linker is

H—Ch—(CH$_2$)$_m$—(CF$_2$)$_n$—R' where Ch stands for chalcogen and is oxygen or sulfur, m is 2–20, n is 2–20, and R' is H or a reactive group that participates in the coupling of the linker to a protein.

17. The antigenic conjugate of claim 16, wherein R' is selected from the group consisting of —CON$_3$, —N$_3$, —CONHNH$_2$, —NHNH$_2$, —NH$_2$, —OH, —OMe, —OEt, —COO—Benzyl and —CF$_3$.

18. The antigenic conjugate of claim 15, wherein the linker is

H—Ch—(CH$_2$)$_m$—NHCO—(CF$_2$)$_n$—R' where Ch stands for chalcogen and is oxygen or sulfur, m is 2–20, n is 2–20, and R' is H or a reactive group that participates in the coupling of the linker to a protein.

19. The antigenic conjugate of claim 18 wherein R is selected from the group consisting of —CON$_3$, —N$_3$, —CONHNH$_2$, —NHNH$_2$, —NH$_2$, —OH, —OMe, —OEt, —COO—Benzyl and —CF$_3$.

20. The antigenic conjugate of claim 18 wherein at least one fluorine atom in said fluorocarbon chain is an F$^{19}$.

21. The antigenic conjugate of claim 13 in which the hapten is a T antigenic determinant.

22. The method of claim 1 in which the hapten is a T-hapten.

23. The method of claim 22 in which the carrier is keyhole limpet hemocyanin.

24. The conjugate of claim 21 in which the carrier is keyhole limpet hemocyanin.

* * * * *

UNITED STATES PATENT AND TRADEMARK OFFICE
CERTIFICATE OF CORRECTION

PATENT NO. : 5,055,562
DATED : October 8, 1991
INVENTOR(S) : R. Rao Koganty

It is certified that error appears in the above-indentified patent and that said Letters Patent is hereby corrected as shown below:

Column 3, line 49  Delete "2,2,2,3,3,4,4 - Hexafluoro", insert therefor -- 2. 2,2,3,3,4,4 - Hexafluoro --

Column 4, line 17  Delete "5O-Galactosyl,", insert therefor -- 5-O-Galactosyl --

Column 4, line 65  Delete "SPEC2RAORE", insert therefor -- SPECTRAPORE --

Column 6, line 49  Delete "Hemocyconin", insert therefor -- Hemocyanin --

Column 8, line 6  Delete "oonjugate", insert therefor -- conjugate --

Signed and Sealed this

Fifteenth Day of November, 1994

Attest:

BRUCE LEHMAN

*Attesting Officer*   *Commissioner of Patents and Trademarks*